US006197207B1

(12) United States Patent
Chapman et al.

(10) Patent No.: US 6,197,207 B1
(45) Date of Patent: Mar. 6, 2001

(54) METHOD OF REDUCING THE POSSIBILITY OF TRANSMISSION OF SPONGIFORM ENCEPHALOPATHY DISEASES BY BLOOD PRODUCTS

(75) Inventors: John Chapman, Lake Villa; Jerry Fisher, Wadsworth, both of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 08/861,859

(22) Filed: May 21, 1997

(51) Int. Cl.$^7$ ............................ B01D 61/14; B01D 21/26; A61M 1/34
(52) U.S. Cl. ............ 210/767; 210/650; 210/651; 210/782; 210/787; 435/2; 604/6.03
(58) Field of Search ................................. 210/645, 767, 210/782, 787, 650, 651; 604/4, 5, 4.01, 5.01, 6.03; 435/2

(56) References Cited

U.S. PATENT DOCUMENTS

| 5,096,906 | * | 3/1992 | Mandell et al. | 514/263 |
|---|---|---|---|---|
| 5,173,415 | * | 12/1992 | Hiratani et al. | 435/183 |
| 5,196,429 | * | 3/1993 | Mandell et al. | 514/263 |
| 5,935,092 | * | 8/1999 | Sun et al. | 604/4 |

FOREIGN PATENT DOCUMENTS

| 97/39227 | * | 10/1997 | (WO) . |
| 97/45746 | * | 12/1997 | (WO) . |
| 97/46572 | * | 12/1997 | (WO) . |
| 98/18908 | * | 5/1998 | (WO) . |

OTHER PUBLICATIONS

Arya, "Creutzfeldt–Jakob Disease and blood transfusion," *Br Med J*, vol. 303, p. 522 (1991).
Bradley, "The Research Programme on Transmissible Spongiform Encephalopathies in Britain With Special Reference to Bovine Spongiform Encephalopathy," *Dev Biol Stand*, vol. 80, pp. 157–170 (1993).
Brown et al, "'Friendly fire' in medicine: hormones, homografts, and Creutzfeldt–Jakob disease", *The Lancet*, vol. 340, pp. 24–27 (1992).
Brown, "Infectious Cerebral Amyloidosis: Clinical Spectrum, Risks and Remedies," *Dev Biol Stand*, vol. 80, pp. 91–101 (1992).
Brown, "Can Creutzfeldt–Jakob disease be transmitted by transfusion?," *Current Opinion in Hematology*, vol. 2, pp. 472–472–477 (1995).
Bruce et al, "Transmission of bovine spongiform encephalopathy and scrapie to mice: strain variation and the species barrier," *Phil. Trans. R. Soc. Lond. B*, vol. 343, pp. 405–411 (1994).
Casaccia et al, "*Levels of infectivity in the blood throughout the incubation period of hamsters peripherally injected with scrapie*," Arch Virol, vol. 108, pp. 145–149 (1989).

Clarke et al, "Presence of the Transmissible Agent of Scrapie in the Serum of Affected Mice and Rats," *The Veterinary Record*, vol. 80, No. 16, p. 504 (1967).
Collinge et al, "Less beef, more brain," *The Lancet*, vol. 347, pp. 915–917 (1996).
Contreras et al, "Creutzfeldt–Jakob Disease and blood transfusion," *Br Med J*, vol. 303, p. 187 (1991).
Dealler, "Bovine Spongiform Encephalopathy (BSE): The Potential Effect of the Epidemic on the Human Population," *British Food Journal*, vol. 95, pp. 22–34 (1993).
Deslys et al, "Selection of specific strains in iatrogenic Creutzfeldt–Jakob disease," *The Lancet*, vol. 343, pp. 848–849 (1994).
Eklund et al, "Pathogenesis of Scrapie Virus Infection in the Mouse," *The Journal of Infectious Diseases*, vol. 117, pp. 15–22 (1967).
Esmonde et al, "Creutzfeldt–Jakob disease and blood transfusion," *The Lancet*, vol. 341, pp. 205–207 (1993).
Field et al, "Scrapie Agent in Blood," *The Veterinary Record*, vol. 83, No. 4, pp. 109–110 (1968).
Gajdusek et al, "Experimental Transmission of a Kuru–Like Syndrome to Chimpanzees," *Nature*, vol. 209, pp. 794–796 (1966).
Gibbs et al, "Creutzfeldt–Jakob Disease (Spongiform Encephalopathy): Transmission to the Chimpanzee," *Science*, vol. 161, pp. 388–389 (1968).
Hadlow et al, "Course of Experimental Scrapie Virus Infection in the Goat," *The Journal of Infectious Diseases*, vol. 129, No. 5, pp. 559–567 (1974).
Heye et al, "Creutzfeldt–Jakob disease and blood transfusion," *The Lancet*, vol. 343, pp. 298–299 (1994).
Kimberlin et al, "Incubation Periods of Six Models of Intraperitoneally Injected Scrapie Depend Mainly on the Dynamics of Agent Replication within the Nervous System and Not the Lymphoreticular System," *J. gen. Virol.*, vol. 69, pp. 2953–2960 (1988).
Kimberlin et al, "Bovine Spongiform Encephalopathy," *Ann NY Acad Sci*, vol. 724, pp. 210–220 (1989).
Klein et al, "Transmission of Creutzfeldt–Jakob Disease by blood transfusion," *The Lancet*, vol. 341, p. 768 (1993).
Kuroda et al, "Creutzfeldt–Jakob Disease in Mice: Persistent Viremia and Preferential Replication of Virus in Low–Density Lymphocytes," *Infection and Immunity*, vol. 41, No. 1, pp. 154–161 (1983).

(List continued on next page.)

*Primary Examiner*—John Kim
(74) *Attorney, Agent, or Firm*—Robert M. Barrett; Denise M. Serewicz; Amy L. H. Rockwell

(57) ABSTRACT

Methods for reducing or preventing the transmission of transmissible spongiform encephalopathy through blood or blood products are provided. The methods require the intact removal of leukocytes that are present in a blood product or an intermediate of a blood product prior to administering the blood product to a patient. To prevent or reduce the transmission of transmissible spongiform encephalopathies disease substantially all leukocytes are removed intact without significant lysis of such leukocytes.

17 Claims, No Drawings

OTHER PUBLICATIONS

Manuelidis, "Transmission of Creutzfeldt–Jakob Disease from Man to the Guinea Pig," *Science*, vol. 190, pp. 571–572 (1975).

Manuelidis et al, "Viremia in Experimental Creutzfeldt–Jakob Disease," *Science*, vol. 200, pp. 1069–1071 (1978).

Manuelidis et al, "Transmission to Animals of Creutzfeldt–Jakob Disease From Human Blood," *The Lancet*, pp. 896–897 (1985).

Manuelidis et al, "Transmission studies from blood of Alzheimer disease patients and healthy relatives," *Proc. Natl. Acad. Sci. USA*, vol. 85, pp. 4898–4901 (1988).

Marsh et al, "Transmissible Mink Encephalopathy: Studies on the Peripheral Lymphocyte," *Infection and Immunity*, vol. 7, pp. 352–355 (1973).

Marsh, "Bovine spongiform encephalopathy: a new disease of cattle?," *Arch Virol* (Suppl), vol. 7, pp. 255–259 (1993).

Morgan, "Blood to be screened to CJD," *BMJ*, vol. 313, p. 441 (1996).

Patterson et al, "Bovine spongiform encephalopathy and the public health," *Journal of Public Health Medicine*, vol. 13, No. 3, pp. 261–268 (1995).

Tamai et al, "Demonstration of the Transmissible Agent in Tissue From a Pregnant Woman with Creutzfeldt–Jakob Disease," *N Eng J Med*, vol. 327, p. 649 (1992).

Tateishi et al, "Experimental Transmission of Human Subacute Spongiform Encephalopathy to Small Rodents," *Acta Neuropathologica*, vol. 51, pp. 127–134 (1980).

Tateishi et al, "Unconventional Pathogens Causing Spongiform Encephalopathies Absent in Blood Products," *Journal of Medical Virology*, vol. 16, pp. 11–15 (1985).

Tateishi, "Transmissible of Creutzfeldt–Jakob Disease From Human Blood and Urine to Mice," *The Lancet*, p. 1074 (1985).

Watkins, "Creutzfeldt–Jakob Disease and blood transfusion," *Br Med J*, vol. 302, p. 1537 (1991).

Contreras et al, "Creutzfeldt–Jakob Disease and blood transfusion," *Br Med J*, vol. 302, p. 11148 (1991).

Diringer, "Sustained Viremia in Experimental Hamster Scrapie," *Archives of Virology*, vol. 82, pp. 105–109 (1984).

Matthews, "BSE: A Mid–Term Report Part 1," *State Vet J*, vol. 2, pp. 8–11 (1992).

Bruisten, S.M. et al., *Efficiency of White Cell Filtration in a Freeze–Thaw Procedure for Removal of HIV–Infected Cells From Blood, Transfusion*, 1990, 30:833–837.*

* cited by examiner

METHOD OF REDUCING THE POSSIBILITY OF TRANSMISSION OF SPONGIFORM ENCEPHALOPATHY DISEASES BY BLOOD PRODUCTS

BACKGROUND OF THE INVENTION

The present invention relates generally to the transmission of diseases. More specifically, the present invention relates to the transmission of spongiform encephalopathy diseases through blood products.

In a variety of therapies, such as transfusions and transplants, body fluids, especially blood components, such as red blood cells, platelets, plasma, and bone marrow, are infused from one or more individuals into a patient. The development of such treatments provide therapies, some of which are life-saving, that cannot otherwise be provided. However, due to the risk of transmission of certain disease states, there may be potential risks with such therapies.

Unfortunately, it is also known that a number of disease states can be transmitted through the infusion of blood products. For example, it is known that blood can carry infectious agents, such as hepatitis virus, human immunodeficiency viruses (an etiological agent for AIDS), cytomegalo virus, Epstein Barr virus, and herpes virus. Much recent effort has been devoted to eliminating the risk of the transmission of hepatitis and acquired immune deficiency syndrome (AIDS) through blood and blood products.

In certain areas of the medical community, recent attention has been focused on transmissible spongiform encephalopathies (TSE). TSE diseases are progressive, lethal central nervous system disorders that are characterized by localized anatomical changes in the brain. These changes consist of vacuoles and protein deposits.

TSE diseases occur in both humans and animals. These neurodegenerative diseases have long latency periods. In humans the latency period can reach up to 30 years. When the disease manifestations finally begin to occur, death usually results within 2 to 4 months; due to the loss of central nervous system function.

TSE diseases can occur: 1) spontaneously; 2) through inheritance; or 3) by iatrogenic exposure to contaminated material. It is believed that the infectious particles responsible for TSE diseases are composed predominantly or perhaps even solely of protein. These proteins have been referred to as prions. It is believed that the infectious prion particles are composed largely, if not entirely, of an abnormal isoform of a normal glycoprotein which is anchored to the external surface of cells. The infectivity of prions has an unconventional property of being unusually resistant to various physio-chemical procedures.

Although TSE diseases have been known for some time, much recent attention has been focused on a new variant of TSE diseases. In March, 1996 Creutzfeldt-Jakob (vCJD) was officially reported. The variant CJD is so called because of the younger ages, than the classical CJD, in which it occurs. Additionally there are also some clinical and pathological differences between the diseases.

There has been some discussion whether there is a link between bovine spongiform encephalopathy ("mad cow disease") and VCJD. Circumstantial evidence suggests exposure to BSE may be the most likely hypothesis for the emergence of vCJD.

Because iatrogenic transmission has been demonstrated with transmissible spongiform encephalopathies including human CJD and vCJD, there may be a question of whether or not such transmissions can occur through blood products. Accordingly, there may be a need for reducing the potential of a risk of the transmission of TSE diseases through blood and/or blood products.

SUMMARY OF THE INVENTION

The present invention provides a method for reducing the risk of the transmission of TSE through blood or blood products. The invention is based on the surprising discovery that the prions that cause TSE reside in the leukocytes. Through the intact removal of the leukocytes the risk of transmission of TSE through blood, blood components, or products made therefrom can be eliminated.

To this end, the present invention provides a method for at least reducing the potential risk for the transmission of transmissible spongiform encephalopathy through blood products comprising the step of removing, intact, substantially all leukocytes that are present in the blood product, or an intermediate of the blood product, prior to administering the blood product to a patient.

In an embodiment, the leukocytes are removed through filtration.

In an embodiment, the leukocytes are removed through centrifugation.

In an embodiment, the blood product is chosen from the group consisting of: whole blood; red blood cell concentrate; plasma; platelet concentrates; pooled platelet concentrates; albumin; gamma globulin; coagulate factors; and cryoprecipate.

In an embodiment, the leukocytes are removed using a size exclusion filter. In a preferred embodiment, the filter comprises at least three membrane filter.

In another embodiment of the present invention, a method of processing blood plasma to prevent the transmission of transmissible spongiform encephalopathies disease is provided. The method comprises the step of removing to a level of not greater than 1 cell/$\mu$l leukocytes that may be present in the blood plasma without lysis of leukocytes.

In a still further embodiment of the present invention, a method for preparing a blood product so as to reduce the risk of the transmission of prion transmissible diseases through the infusion of the blood products is provided. The method comprising the steps of: collecting blood plasma; removing intact leukocytes from the blood plasma product without causing the lysis of leukocytes; and preparing a blood product from the blood plasma.

Accordingly, an advantage of the present invention is to reduce the risk of the transmission of TSE diseases.

Moreover, an advantage of the present invention is to reduce the risk of transmission of TSE diseases through blood and blood products.

Still an advantage of the present invention is to reduce the risk of transmission of prions through blood or blood products.

Further, an advantage of the present invention is to provide a method for insuring that TSE diseases are not transferred through the use of blood and/or blood products.

These and other features and advantages of the present invention are set forth in detail below in the detailed description of the presently preferred embodiments.

DETAILED DESCRIPTION OF THE PRESENTLY PREFERRED EMBODIMENTS

The present invention provides a method for reducing any potential risk for the transmission of TSE diseases including vCJD through the use of blood and/or blood products.

The inventors hypothesized that there may be a potential for the transmission of TSE diseases, specifically CJD and vCJD, through blood products. In part, the uncertainty as to the transmissibility of TSE diseases, especially CJD and vCJD, stems from the lack of data regarding the infectious potential of blood from patients with CJD or vCJD.

However, the inventors have considered the relationship of TSE and specifically CJD to agents that previously have been transmitted through blood products. In this regard, the following analysis suggests the potential for the transmission of CJD and vCJD through blood products:

| Characteristics of Agents Effectively Transmitted by Blood, Blood Components and Blood Derivatives | Relevance to Transmissible Spongiform Encephalopathies |
| --- | --- |
| The disease causing agent is present in blood at a titer capable of transmitting the disease. | Data generated in laboratory animals has provided suggestive information that the agent can be present in blood. However, definitive qualitative and quantitative data is lacking for naturally occurring human disease. |
| The transmissible agent causes a disease with a significant asymptomatic incubation period between the time of exposure to the agent and the time of disease manifestation. This time span is called a window period. | These diseases have extraordinary long window periods measured in years instead of weeks as for conventional infectious agents. |
| The transmissible agent is resistant or not susceptible to the processes used in the preparation of blood, blood components or blood derivatives. | These agents have extraordinary resistance to conventional techniques of pathogen inactivation employed in current processing of blood and its derivatives. |
| The transmissible agent is not identified by diagnostic assays used to screen blood for the presence of transmissible agents. | There is currently no diagnostic test that can detect the presence of the transmissible agent in blood. |
| Donors who are carrying the transmissible agent are not identified reliably with current interviews and health assessments employed. | Some donors groups who are at a higher risk of having this type of disease have been identified and are excluded as donors. These higher risk individuals cannot always be identified during an interview process. |

Based upon this analysis, a potential but unproven risk exists for the transmission of TSE diseases by blood or its derivatives. During this period of uncertainty, it is perhaps appropriate to identify measures that can be introduced into the processing of blood and its derivatives to minimize any potential risk.

To this end, pursuant to the present invention, methods are provided for the processing of blood, e.g., plasma intended to be used for the preparation of fresh and frozen plasma and plasma fractions and derivatives for therapeutic purposes. It is believed that these methods will reduce the risk of transmitting TSE diseases by these products.

The inventors have surprisingly discovered a link between cells of the lymphoid tissues and the pathogenesis of TSE diseases. In this regard, studies have demonstrated that the agent capable of transmitting TSE diseases (prions) can be present in lymphoid tissues such as spleen, thymus, lymph nodes, and Peyer's patches, as well as in the buffy coat of blood preparations.

Unexpectedly, it is possible to substantially remove all transmissible agents causing TSE diseases from the blood or render it substantially incapable of transmitting this type of disease. To this end, pursuant to the present invention, the blood product, or one of its intermediates, is treated with a leukodepletion process.

As used herein blood product includes: e.g., whole blood, red blood cell concentrate, plasma, platelet concentrates, pooled platelet concentrate, and therapeutic products made from blood or any of its components, e.g., albumin, gamma globulin, coagulatic factors, cryo-precipitate, etc.

Pursuant to the present invention, the leukodepletion process preferably removes leukocytes to fewer than 1 cell/$\mu$l (the current level of detection). In an embodiment, the leukodepletion process is performed using filtration processes based upon a size exclusion principle. Leukocytes are removed from the liquid plasma by passing the plasma through a defined media of known porosity.

An example of a filter that can be used pursuant to the present invention is disclosed in U.S. patent application Ser. No. 08/841,163, abandoned, entitled "Method for Purifying Blood Plasma and Apparatus Suitable Therefor", filed on Apr. 29, 1997, the disclosure of which is hereby incorporated herein by reference. Generally the filter is a steam sterilizable multi-element filter assembly comprising a housing, preferably of sterilizable polymer having inlet and outlet portions, the inlet portion including an inlet port and the outlet portion including an outlet port, the inlet and outlet portions including a flow channel between the inlet and outlet ports; one or more prefilter(s) retained within the housing fully extending across the flow channel, the prefilter(s) disposed closer to the inlet port than the outlet port; two or more hydrophilic microporous membrane(s) retained within and preferably hermetically sealed to the housing and extending across the flow channel, an intermediate hydrophilic microporous membrane adjacent to the prefilter and disposed closer to the outlet port than the inlet port and at least a final hydrophilic microporous membrane adjacent the intermediate membrane; such that plasma to be purified must pass in order through the prefilter(s), the intermediate hydrophilic microporous membrane, and then the final hydrophilic microporous membrane.

In another embodiment, the leukocytes are removed through a centrifugation process.

In any such process the leukocytes must be removed intact. Cell lysis must be avoided. If the leukocytes are disrupted, the prions contained therein will then become extra-cellular creating the potential for the transmissions of TSE disease by the resultant blood product.

Accordingly, in a filtration process, the filter must be designed to avoid a cell lytic effect. Furthermore, such filtration must take place prior to the cells becoming lysed due to any reason. Such lysis can occur as a result of spontaneous degradation (autolysis), as a result of mechanical trauma (e.g., freeze-thaw processes), or by membrane solubization due to the treatment of the cells or cell debris with chemicals used in the preparation of blood (e.g., solvents and detergents). Thus, the preparation of the blood and filtration process must proceed so as to avoid any of these potential lysis prior to the removal of the leukocytes.

This method of preventing the transmission of TSE, and decontaminating blood products that may contain same, is based on the recognition that cellular elements, particularly leukocytes, are the compartment in blood that the relevant prion protein resides. Once these blood cells are disrupted by spontaneous autolysis processes, by mechanical disruption associated with freezing-thawing plasma, or by the treatment with chemical agents—such as solvents and detergents employed in manufacturing blood derivatives—the agent causing transmissible TSE will not be removed.

By way of example and not limitation, examples of the process of the present invention will now be set forth.

A. For fresh frozen plasma and for blood products derived from human plasma (albumin, gamma globlulin, coagulation factor concentrates, cryoprecipitate, fibrin glue, etc.).

1. Plasma is collected from whole blood using conventional methods of separation based upon centrifugation or membrane technology.

2. Prior to freezing and within 10 hours of plasma collection, and preferably within 4 hours of plasma collection, the plasma is leukodepleted to a level of fewer than 1 cell/$\mu$l (current level of sensitivity of leukocyte detection methodologies). The method of leukodepletion must be non-destructive to the leukocytes.

3. Leukodepletion can be achieved using a leukocyte removal filter. The leukocyte removal filter preferentially operates on the basis of size exclusion in which the plasma passes through a membrane or layers of membranes which act as a sieve to remove particles greater than 2 microns in size and preferably removing particle greater than 0.8 microns in size. The pore size of the membrane should be minimized to the extent possible such that an adequate flow characteristics of the filter can be maintained, it minimizes inducing shear forces which would lyse leukocytes and therapeutic proteins of interest are not retained by the filtration process. A suitable filter is discussed above.

4. The leukodepletion step must be carried out prior to freezing and thawing the plasma.

5. The leukodepletion step must not cause significant cell lysis. The filtration step must minimize the production of cell membrane fragments and preferably removes membrane fragments potentially generated during the plasma collection process.

6. The leukodepletion step must not result in the loss of greater than 10 and preferably less than 1% of plasma proteins of therapeutic importance including albumin and Factor VIII.

7. The leukodepletion step must not result in the activation of plasma protein cascades including the coagulation system of the complement system.

8. The leukodepletion step must be compatible with blood banking operations. The maximum time for filtering 900 ml of plasma is 1 hour and preferably less than 20 minutes.

9. The leukodepletion step can be either an integral component of a plasma collection system with leukodepletion conducted concurrently with plasma collection from the donor (on-line procedure) or it can be conducted after the plasma is collected from the donor (off-line procedure).

10. The plasma to be treated with the process can be derived by autopheresis procedure or be recovering plasma from units of whole blood.

B. For animal derived biologics used in cell culture (e.g., fetal bovine serum, horse serum, calf serum, etc.). The preparation of the serum should be modified to include a leukodepletion step as described above prior to the induction of the clotting process of the plasma.

It should be understood that various changes and modifications to the presently preferred embodiments can be made. Such changes and modifications are intended to be encompassed by the following claims.

We claim:

1. A method for at least reducing the potential risk for the transmission of transmissible spongiform encephalopathy through blood products comprising the step of removing, intact, substantially all leukocytes that are present in the blood product, or an intermediate of the blood product, without causing the lysis of the leukocytes, the leukocytes being removed prior to administering the blood product to a patient.

2. The method of claim 1 wherein the leukocytes are removed through filtration.

3. The method of claim 1 wherein the leukocytes are removed through centrifugation.

4. The method of claim 1 wherein the blood product is chosen from the group consisting of: whole blood; red blood cell concentrate; plasma; platelet concentrates; pooled platelet concentrates; albumin; gamma globulin; coagulate factors; and cryo-precipitate.

5. The method of claim 2 including the step of passing the blood product, or the intermediate of the blood product, through a size exclusion filter to remove the leukocytes.

6. The method of claim 1 including the step of passing the blood product, or the intermediate of the blood product, through a multi-element filter including at least three filter membranes to remove the leukocytes.

7. A method of processing blood plasma to prevent the transmission of transmissible spongiform encephalopathies disease through the blood plasma, or any product derived therefrom, comprising the step of removing to a level of not greater than 1 cell/$\mu$l leukocytes that may be present in the blood plasma without significant lysis of leukocytes.

8. The method of claim 7 wherein the leukocytes are removed through filtration.

9. The method of claim 7 wherein the leukocytes are removed through centrifugation.

10. The method of claim 7 including the step of passing the blood plasma through a size exclusion filter to remove the leukocytes.

11. The method of claim 7 including the step of passing the blood plasma through a multi-element filter including at least three filter membranes to remove the leukocytes.

12. A method for preparing a blood product so as to reduce the risk of the transmission of prion transmissible diseases through the infusion of the blood product comprising the steps of:

collecting blood plasma;

removing intact leukocytes from the blood plasma product without causing the lysis of leukocytes; and preparing a blood product from the blood plasma.

13. The method of claim 12 wherein the leukocytes are removed through filtration.

14. The method of claim 12 wherein the leukocytes are removed through centrifugation.

15. The method of claim 12 wherein the blood product is chosen from the group consisting of whole blood; red blood cell concentrate; plasma; platelet concentrates; pooled platelet concentrates; albumin; gamma globulin; coagulate factors; and cryo-precipitate.

16. The method of claim 12 including the step of passing the blood plasma through a size exclusion filter to remove the leukocytes.

17. The method of claim 12 including the step of passing the blood plasma through a multi-element filter including at least three filter membranes to remove the leukocytes.

* * * * *